United States Patent
Tung-Sing Pak et al.

(10) Patent No.: US 8,041,106 B2
(45) Date of Patent: Oct. 18, 2011

(54) METHODS AND SYSTEMS FOR DETECTING DEFECTS ON A RETICLE

(75) Inventors: Patrick Tung-Sing Pak, Singapore (SG); Wee-Teck Chia, Singapore (SG); Aaron Geurdon Chin, Singapore (SG); Irfan Malik, Sunnyvale, CA (US); Brian Duffy, San Jose, CA (US)

(73) Assignee: KLA-Tencor Corp., San Jose, CA (US)

( * ) Notice: Subject to any disclaimer, the term of this patent is extended or adjusted under 35 U.S.C. 154(b) by 521 days.

(21) Appl. No.: 12/328,862

(22) Filed: Dec. 5, 2008

(65) Prior Publication Data

US 2010/0142800 A1    Jun. 10, 2010

(51) Int. Cl.
*G01K 9/00* (2006.01)
(52) U.S. Cl. ..... 382/149; 382/144; 382/145; 356/237.2; 356/237.5
(58) Field of Classification Search ............... 382/144, 382/145, 151, 148, 149; 356/237.2, 237.4, 356/237.5
See application file for complete search history.

(56) References Cited

U.S. PATENT DOCUMENTS

| | | | |
|---|---|---|---|
| 6,902,855 B2 | 6/2005 | Peterson et al. | |
| 7,769,225 B2 * | 8/2010 | Kekare et al. | 382/145 |
| 7,796,804 B2 * | 9/2010 | Bhaskar et al. | 382/145 |
| 2004/0130711 A1 | 7/2004 | Werf | |
| 2006/0291714 A1 | 12/2006 | Wu et al. | |
| 2007/0035728 A1 | 2/2007 | Kekare et al. | |
| 2007/0156379 A1 | 7/2007 | Kulkarni et al. | |
| 2007/0288219 A1 | 12/2007 | Zafar et al. | |
| 2008/0259323 A1 | 10/2008 | Hirano et al. | |

OTHER PUBLICATIONS

International Search Report for PCT/US2009/066461, mailed Jun. 23, 2010.
U.S. Appl. No. 60/974,030 (Bhaskar et al.) entitled Systems and Methods for Creating Persistent Data for a Wafer and for Using Persistent Data for Inspection-Related Functions filed on Sep. 20, 2007.
U.S. Appl. No. 11/139,151 (Volk) entitled Methods and Systems for Detecting Changes in Reticle Defectivity Over Time filed on May 27, 2005.

* cited by examiner

*Primary Examiner* — Layla Lauchman
(74) *Attorney, Agent, or Firm* — Ann Marie Mewherter

(57) ABSTRACT

Methods and systems for detecting defects on a reticle are provided. One method includes printing a single die reticle in first areas of a wafer using different values of a parameter of a lithography process and at least one second area using a nominal value of the parameter. The method also includes acquiring first images of the first areas and second image(s) of the at least one second area. In addition, the method includes separately comparing the first images acquired for different first areas to at least one of the second image(s). The method further includes detecting defects on the reticle based on first portions of the first images in which variations in the first images compared to the at least one second image are greater than second portions of the first images and the first portions that are common to two or more of the first images.

20 Claims, 3 Drawing Sheets

METHODS AND SYSTEMS FOR DETECTING DEFECTS ON A RETICLE

BACKGROUND OF THE INVENTION

1. Field of the Invention

The present invention generally relates to methods and systems for detecting defects on a reticle. Certain embodiments relate to a method for detecting crystal growth defects on a single die reticle.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

The terms "reticle" and "mask" are used interchangeably herein. A reticle generally includes a transparent substrate such as glass, borosilicate glass, and fused silica having patterned regions of opaque material formed thereon. The opaque regions may be replaced by regions etched into the transparent substrate. Many different types of reticles are known in the art, and the term reticle as used herein is intended to encompass all types of reticles.

A process for manufacturing a reticle is in many ways similar to a wafer patterning process. For example, generally, the goal of reticle manufacturing is forming a pattern on a substrate. In this manner, reticle manufacturing may include a number of different steps such as pattern generation, which may include exposing a substrate having a resist layer formed thereon to a light source in a predetermined pattern. Alternatively, reticles may be patterned by e-beam direct write exposure. After the exposure steps, the reticle is processed through development, inspection, etch, strip, and inspection steps to complete the pattern transfer process. Defects in reticles are a source of yield reduction in integrated circuit (IC) manufacturing. Therefore, inspection of a reticle is a critical step in reticle manufacturing processes.

Once a reticle is fabricated and inspected, it may be qualified as acceptable for manufacturing and released to manufacturing. During the normal course of the life of a reticle, however, defects can be introduced into the reticle. For example, after some exposures using reticles, particularly with deep ultraviolet (DUV) light, defects can appear on the reticles that can be traced back to crystalline defects growing on previously defect free reticle surfaces including those reticle surfaces that are protected by a pellicle. Such crystalline defects are also commonly referred to as "haze defects" or "reticle haze" because areas of the reticle containing such defects appear hazy. Reticle haze may occur when a cloudy substance forms as a result of airborne molecular contaminants reacting with moisture in the environment of the reticle. For example, it is possible that haze may be formed on reticles due to cleaning procedures conducted during the reticle manufacturing process. In addition, or alternatively, haze may be caused by the presence and concentration of airborne molecular contaminants in the manufacturing fabrication facility in which the reticle is being used. Regardless of the cause of reticle haze, the cost of haze defects on reticles can be exorbitant (e.g., in the millions of dollars) and is particularly problematic in fabrication facilities with DUV lithography tools. Accordingly, many manufacturers periodically image or otherwise test reticles to ensure that they are not defective.

The type of inspection, whether for qualification or re-qualification purposes, that can be performed for a reticle varies depending on the reticle itself. For example, some reticles include only a single die, while other reticles include more than one identical die. In instances in which a reticle includes more than one identical die, images or other output generated by an inspection system for one die can be compared to images or the other output for another die on the same reticle. Such "die-to-die" inspection is substantially effective, efficient, and inexpensive. Obviously however, such "die-to-die" inspection cannot be performed for a reticle that has only one die. In contrast, one common inspection method for detecting defects on a single die reticle involves using a reticle inspection system (such as one of those that are commercially available from KLA-Tencor, San Jose, Calif.) to inspect the reticle directly (e.g., by comparing light transmitted by the reticle to light reflected by the reticle on a location-by-location basis). However, although such reticle inspection systems are effective and have achieved great success commercially, such reticle inspection systems do have some disadvantages for some applications in that the reticle inspection systems have relatively high cost of ownership and relatively slow throughput.

Accordingly, it would be advantageous to develop methods and systems for detecting defects on a reticle, and particularly a single die reticle, that are effective, efficient, and inexpensive and are particularly suitable for applications such as reticle re-qualification for which there is typically little or no reticle inspection system availability.

SUMMARY OF THE INVENTION

The following description of various embodiments of methods and systems is not to be construed in any way as limiting the subject matter of the appended claims.

One embodiment relates to a method for detecting defects on a reticle. The method includes printing a reticle in first areas on a wafer and at least one second area on the wafer. The reticle is printed in different first areas using different values of a parameter of a lithography process. The reticle is printed in the at least one second area using a nominal value of the parameter. The reticle is a single die reticle. The method also includes acquiring first images of the first areas and one or more second images of the at least one second area using a wafer inspection system.

The method further includes separately comparing the first images acquired for different first areas to at least one of the one or more second images to determine variation in the first images compared to the at least one second image. In addition, the method includes detecting defects on the reticle based on first portions of the first images in which the variations are greater than second portions of the first images and the first portions that are common to two or more of the first images. The defects include crystal growth defects on the reticle.

In one embodiment, the parameter includes dose. In another embodiment, the parameter includes focus. In an additional embodiment, the method includes printing the reticle in third areas on the wafer. The reticle is printed in different third areas using different values of an additional parameter of the lithography process. The method also includes acquiring third images of the third areas using the wafer inspection system, separately comparing the third images acquired for different third areas to at least one of the one or more second images to determine variation in the third images compared to the at least one second image, and detecting the defects on the reticle based on first portions of the third images in which the variations are greater than second portions of the third images and the first portions of the third images that are common to two or more of the third images. In one such embodiment, the parameter includes dose, and the additional parameter includes focus.

In one embodiment, the first areas are arranged in one column on the wafer, and the at least one second area is arranged in one or more additional columns on the wafer. In another embodiment, the first areas correspond to different dies on the wafer, the at least one second area corresponds to at least one additional die on the wafer, and separately comparing the first images acquired for the different first areas to the at least one second image includes comparing one of the different dies to one of the at least one additional die. In an additional embodiment, the first areas correspond to different dies on the wafer, the at least one second area corresponds to at least two additional dies on the wafer, and separately comparing the first images acquired for the different first areas to the at least one second image includes comparing one of the different dies to two of the additional dies.

In one embodiment, the variations include variations in critical dimensions (CDs) of features in the first images compared to CDs of the features in the at least one second image. In another embodiment, detecting the defects includes comparing locations of the first portions within the first images to identify the first portions that are common to the two or more of the first images.

In one embodiment, detecting the defects includes detecting potential defects on the reticle based on the first portions and the first portions that are common to the two or more of the first images and reviewing locations on the wafer corresponding to the first portions that are common to the two or more of the first images to determine if the potential defects are real defects. In another embodiment, detecting the defects includes comparing locations of the first portions in the first images to locations of patterned features in the first images that correspond to patterned features on the reticle to separate the first portions that correspond to the crystal growth defects from the first portions that correspond to other defects on the reticle. In an additional embodiment, detecting the defects includes performing design based binning of the first portions to separate the crystal growth defects from other defects on the reticle.

In one embodiment, the method is performed subsequent to release of the reticle to manufacturing and use of the reticle in manufacturing. In another embodiment, the defects do not include defects in patterned features on the reticle. In an additional embodiment, the crystal growth defects include crystal growth defects that print on the wafer at the nominal value of the parameter. In a further embodiment, the crystal growth defects include crystal growth defects that will print in almost 100% of the dies printed on wafers with the reticle at the nominal value of the parameter. In still another embodiment, the defects appear in the first images and the one or more second images.

Each of the steps of each of the embodiments of the method described above may be further performed as described herein. In addition, each of the embodiments of the method described above may include any other step(s) of any other method(s) described herein. Furthermore, each of the embodiments of the method described above may be performed by any of the systems described herein.

Another embodiment relates to a computer-implemented method for detecting defects on a reticle. The computer-implemented method includes acquiring first images of first areas on a wafer. The first images are generated by a wafer inspection system. A reticle is printed in different first areas using different values of a parameter of a lithography process. The reticle is a single die reticle. The computer-implemented method also includes acquiring one or more second images of at least one second area on the wafer. The one or more second images are generated by the wafer inspection system. The reticle is printed in the at least one second area using a nominal value of the parameter.

The computer-implemented method further includes separately comparing the first images acquired for different first areas to at least one of the one or more second images to determine variation in the first images compared to the at least one second image. In addition, the computer-implemented method includes detecting defects on the reticle based on first portions of the first images in which the variations are greater than second portions of the first images and the first portions that are common to two or more of the first images. The defects include crystal growth defects on the reticle.

Each of the steps of the computer-implemented method described above may be further performed as described herein. In addition, the computer-implemented method may include any other step(s) of any other method(s) described herein.

An additional embodiment relates to a wafer inspection system configured to detect defects on a reticle. The system includes an inspection subsystem configured to acquire first images of first areas on a wafer and one or more second images of at least one second area on the wafer. A reticle is printed in different first areas using different values of a parameter of a lithography process. The reticle is printed in the at least one second area using a nominal value of the parameter. The reticle is a single die reticle. The system also includes a computer subsystem configured to separately compare the first images acquired for different first areas to at least one of the one or more second images to determine variation in the first images compared to the at least one second image and to detect defects on the reticle based on first portions of the first images in which the variations are greater than second portions of the first images and the first portions that are common to two or more of the first images. The defects include crystal growth defects on the reticle. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

Figure 1:
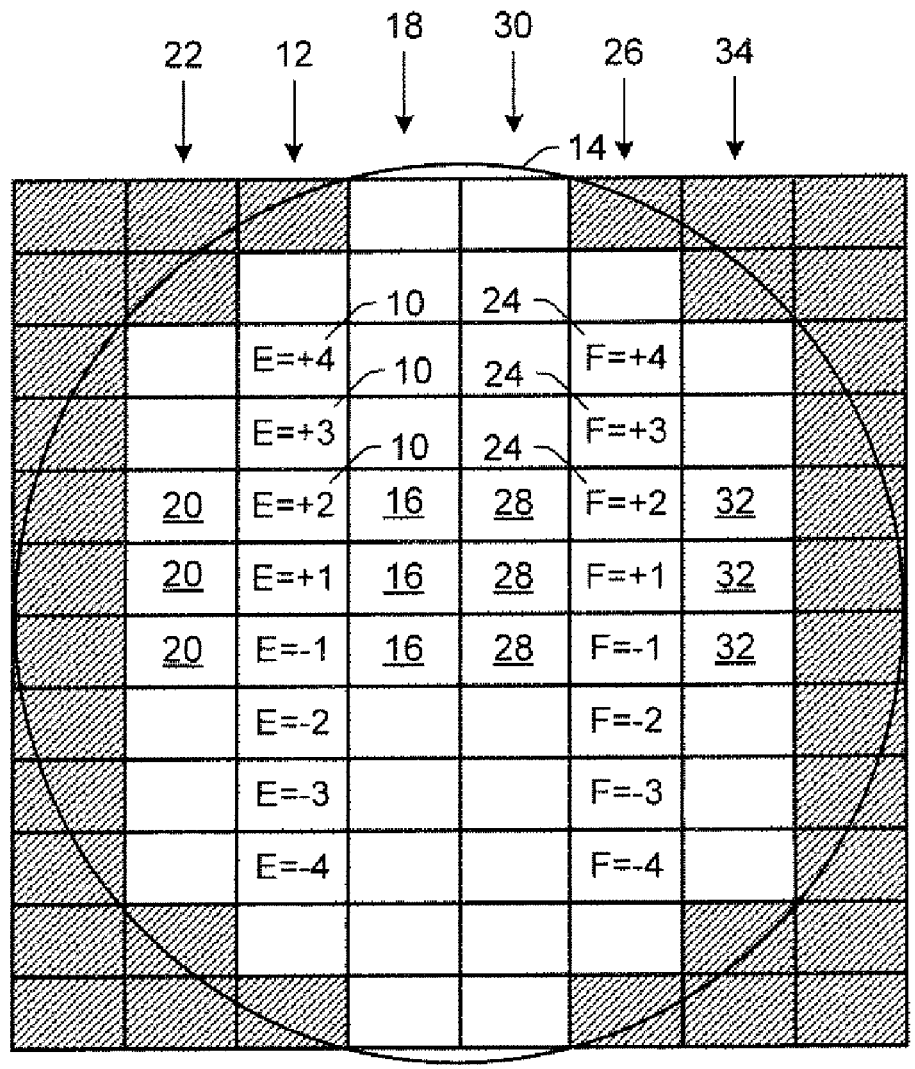
FIG. 1 is a schematic diagram illustrating a plan view of one embodiment of first areas and at least one second area on a wafer in which a reticle may be printed according to embodiments described herein.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable patterned features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to a method for detecting defects on a reticle. The method includes printing a reticle in first areas on a wafer and at least one second area on the wafer. The reticle is printed in different first areas using different values of a parameter of a lithography process. Each of the different first areas may correspond to a different "shot" of the reticle on the wafer. In addition, the different value of the parameter may be modulated from shot to shot on the wafer. In this manner, the method may include printing modulated shots on the wafer with varying values of a parameter of the lithography process. The reticle is printed in the at least one second area using a nominal value of the parameter. As such, the method includes preparing a print-down wafer with one of the layouts described further herein.

In one embodiment, the parameter includes dose. In particular, the parameter may include the dose at which the wafer is exposed using the reticle. In another embodiment, the parameter includes focus. In particular, the parameter may include the focus at which the wafer is exposed using the reticle. In this manner, the parameter of the lithography process may be an exposure parameter of the lithography process. The different values of the parameter may include any of the different values described herein. In addition, the nominal value may include the best known value for the parameter or some predetermined value for the parameter. For example, if the exposure system used in the lithography process is known to operate best at a focus of 0 µm, the nominal value for focus may be 0 µm.

In this manner, printing the reticle on the wafer in the embodiments described herein is similar to how a reticle is printed on a wafer in the process window qualification (PWQ) methodology that is used to detect marginal designs and lithography process margins on clean reticles. The PWQ methodology is described in detail in commonly owned U.S. Pat. No. 6,902,855 to Peterson et al., which is incorporated by reference as if fully set forth herein. The embodiments described herein may include any step(s) of any method(s) described in this patent.

In one embodiment, the first areas are arranged in one column on the wafer. In this manner, the method may include printing a column of modulated shots on the wafer with different values of a parameter of a lithography process. For example, FIG. 1 illustrates first areas and at least one second area on a wafer in which a reticle may be printed according to embodiments described herein. As shown in FIG. 1, first areas 10 may be arranged in column 12 on wafer 14. The parameter of the lithography process at which first areas 10 shown in FIG. 1 are printed with different values is dose. For example, as shown in FIG. 1, one of the different first areas may be printed with a nominal value of dose +4 mJ/cm$^2$ ("E=+4"), another of the different first areas may be printed with a nominal value of dose +3 mJ/cm$^2$ ("E+3"), another of the different first areas may be printed with a nominal value of dose +2 mJ/cm$^2$ ("E=+2"), . . . and another of the different first areas may be printed with a nominal value of dose −4 mJ/cm$^2$ ("E=−4"). In this manner, the dose may be varied in increments of 1 mJ/cm$^2$ from one first area to the next. However, the dose may be varied in any other suitable increments across any suitable range of dose. In addition, the different values may be selected such that some of the first areas are overexposed (e.g., E=+4, E=+3, etc.) and such that some of the first areas are underexposed (e.g., E=−4, E=−3, etc.).

The at least one second area may be arranged in one or more additional columns on the wafer. For example, as shown in FIG. 1, second areas 16 may be arranged in column 18 on wafer 14. The reticle may be printed in each of second areas 16 at the same nominal value of dose if the first areas are printed at different, modulated values of dose. As shown in FIG. 1, column 18 may include different second areas 16, and each of the second areas may be used as described herein for the first area in the same row as each of the second areas. Such an arrangement is advantageous because a first area and a second area in the same row on the wafer can be scanned sequentially by the wafer inspection system, and the images generated during scanning can be compared as described further herein. However, column 18 may include only one second area. Column 18 may also include more than one second area and fewer second areas than the number of first areas in column 12.

The at least one second area may also or alternatively be arranged in a different additional column on the wafer. For example, as shown in FIG. 1, second areas 20 may be arranged in column 22 on wafer 14. The reticle may be printed in each of second areas 20 at the same nominal value of dose if the first areas are printed at different, modulated values of dose. As shown in FIG. 1, column 22 may include different second areas 20, and each of the second areas may be used as described herein for the first area in the same row as each of the second areas. Such an arrangement is advantageous as described above. However, column 22 may include only one second area. Column 22 may also include more than one second area and fewer second areas than the number of first areas in column 12. Each of first areas 10, second areas 16, and second areas 20 may be printed at the same value of other parameters of the lithography process (e.g., focus).

The reticle is a single die reticle. For example, a reticle may include a single die when the size of a die prevents more than one identical die from fitting on a single reticle. A single die on a reticle may be used to fabricate a single device. However, a single die on a reticle may be used to fabricate multiple, different devices. For example, a single die on a reticle may include patterned features that are used to fabricate multiple, different devices on wafers. Although the embodiments described herein are particularly useful for detecting defects on a single die reticle as described further herein, the embodiments described herein can also be used to detect defects on non-single die reticles (i.e., multi-die reticles).

In one embodiment, the first areas correspond to different dies on the wafer. For example, the reticle may be printed once (e.g., only once) in each of the different first areas on the wafer. In this manner, the die on the reticle may be printed once (e.g., only once) in each of the different first areas on the wafer. As such, the die on the reticle may be printed in each of the different first areas on the wafer. In one such embodiment, the at least one second area corresponds to at least one additional die on the wafer. The at least one second area may correspond to at least one additional die on the wafer as described above. In this manner, the first areas and the at least one second area may correspond to different dies on the wafer. In another such embodiment, the at least one second area corresponds to at least two additional dies on the wafer. The at least one second area may correspond to at least two additional dies on the wafer as described above. For example, the reticle may be printed in two different second areas on the wafer, each of which thereby corresponds to one die on the wafer. In this manner, each of the first areas and each of the second area(s) printed on the wafer may correspond to a different die on the wafer.

As described above, the reticle may be printed in different areas on the wafer using different values of at least one parameter of a lithography process. For example, if the reticle is printed using the layout shown in FIG. 1, the reticle may be printed in first areas 10 in column 12 using different values of dose. In this manner, there may be at least one column of varying dose printed on the wafer. However, the reticle may be printed in other different areas on the same wafer using different values of an additional parameter of the lithography process. For example, in some embodiments, the method includes printing the reticle in third areas on the wafer. The reticle is printed in different third areas using different values of an additional parameter of the lithography process. In this manner, the method may include printing modulated shots on the wafer with varying values of two different parameters of the lithography process. The third areas may be arranged on the wafer as described above. For example, the first areas may be arranged in one column on the wafer, and the third areas may be arranged in a different column on the wafer.

FIG. 1 also illustrates third areas on the wafer in which a reticle may be printed according to embodiments described herein. As shown in FIG. 1 third areas 24 may be arranged in column 26 on wafer 14. The parameter of the lithography process at which third areas 24 shown in FIG. 1 are printed with different values is focus. For example, as shown in FIG. 1, one of the different third areas may be printed with a nominal value of focus +4 µm ("F=+4"), another of the different third areas may be printed with a nominal value of focus +3 µm ("F=+3"), another of the different third areas may be printed with a nominal value of focus +2 µm ("F=+2"), . . . and another of the different third areas may be printed with a nominal value of exposure dose −4 µm ("F=−4"). In this manner, the wafer may include at least one column of varying dose and an optional column of varying focus. As shown in FIG. 1, the focus may be varied in increments of 1 µm from one third area to the next. However, the focus may be varied in any other suitable increments across any suitable range of values of focus. In addition, the reticle may be printed in some of the third areas at different values of positive defocus (e.g., F=+4, F=+3, etc.) and some of the third areas at different values of negative defocus (e.g., F=−4, F=−3, etc.).

In addition, at least one second area 28 may be arranged in column 30 on wafer 14. The reticle may be printed in each of second areas 28 at the same nominal value of focus if the third areas are printed at different, modulated values of focus. As shown in FIG. 1, column 30 may include different second areas 28, and each of the second areas may be used as described herein for the third area in the same row as each of the second areas. Such an arrangement is advantageous as described above. However, column 30 may include only one second area. Column 30 may also include more than one second area and fewer second areas than the number of third areas in column 24. Therefore, as shown in FIG. 1, there may be at least two columns 18 and 30 printed at nominal conditions between the two modulated columns 12 and 26. Each of those two columns may be used as described herein for a different modulated column. Alternatively, both of those two columns may be used as described herein for both modulated columns.

In addition, or alternatively, at least one second area 32 may be arranged in column 34 on wafer 14. The reticle may be printed in each of second areas 32 at the same nominal value of focus if the third areas are printed at different, modulated values of focus. As shown in FIG. 1, column 34 may include different second areas 32, and each of the second areas may be used as described herein for the third area in the same row as each of the second areas. Such an arrangement is advantageous as described above. However, column 34 may include only one second area. Column 34 may also include more than one second area and fewer second areas than the number of third areas in column 26. Each of third areas 24, second areas 28, and second areas 32 may be printed at the same value of other parameters of the lithography process (e.g., dose). Furthermore, all of the second areas on the wafer may be printed at the same nominal value of dose and the same nominal value of focus. The shaded rectangles shown in FIG. 1 illustrate areas on the wafer in which only a portion of the reticle may be printed and areas located outside of the area of the wafer in which the reticle cannot be printed.

In this manner, the method may include printing different columns of modulated shots on the wafer with different values of two parameters of a lithography process. In addition, the third areas may correspond to different dies on the wafer (i.e., dies different than the dies corresponding to the first areas and dies different than the die(s) corresponding to the at least one second area). In one such embodiment, the parameter includes dose, and the additional parameter includes focus. In this manner, the method may include printing different columns of modulated shots on a wafer with varying dose and focus.

The method also includes acquiring first images of the first areas and one or more second images of the at least one second area using a wafer inspection system. The wafer inspection system may be a commercially available wafer inspection system such as the 2350 tools and 28xx tools, which are commercially available from KLA-Tencor, San Jose, Calif. The wafer inspection system may be configured for inspection of patterned wafers. In addition, the wafer inspection system may be configured for bright field (BF) inspection. Furthermore, the wafer inspection system may be configured as an optical inspection system. Acquiring the first images and the one or more second images using the wafer inspection system may be performed in any suitable manner. For example, acquiring the first images and the one or more second images using the wafer inspection system may be performed by scanning the wafer. Scanning the wafer may include moving the wafer (by a stage of the wafer inspection system on which the wafer is located) with respect to optics of the wafer inspection system such that the illumination of the wafer inspection system traces a serpentine path over the wafer as light reflected from the wafer is detected by the wafer inspection system. The first images and the one or more second images may be acquired in the same scan of the wafer.

In one embodiment, the method includes acquiring third images of the third areas using the wafer inspection system. Acquiring the third images of the third areas using the wafer inspection system may be performed as described further herein with respect to acquiring first images of the first areas using the wafer inspection system. In addition, the first images and the third images may be acquired in the same scan of the wafer.

The method also includes separately comparing the first images acquired for different first areas to at least one of the one or more second images to determine variation in the first images compared to the at least one second image. Separately comparing the first images acquired for different first areas to at least one of the one or more second images may be performed by comparing a first image of a first area in one row on the wafer to a second image of a second area in the same row on the wafer. Alternatively, separately comparing the first images acquired for different first areas to at least one of the one or more second images may be performed by separately comparing different first images acquired for different first areas to one or more second images. In any case, the first images acquired for different first areas may be separately compared to the at least one second image such that the variation in each of the first images that is compared can be separately determined. In this manner, variation within each of the first images can be separately determined with respect to an image of an area exposed at the nominal value of the modulated parameter. Separately comparing the images may also include aligning the first images to the at least one second image and performing any other functions that facilitate the comparison of the images on a location by location basis.

The characteristics of the first images and the at least one second image that are compared may include any measurable characteristics of the images such as critical dimension (CD) of features that appear in the images. Such variations may be determined in any suitable manner as a function of position within the images.

As described above, in one embodiment, the first areas correspond to different dies on the wafer, and the at least one second area corresponds to at least one additional die on the wafer. In one such embodiment, separately comparing the first images acquired for the different first areas to the at least one second image includes comparing one of the different dies to one of the at least one additional die. In this manner, separately comparing the first images to the at least one second image may include performing a number of different die-to-die comparisons (e.g., one comparison for each of the different first areas being compared). As such, acquiring the first images and the one or more second images and separately comparing the first images to the at least one second image may be performed in a manner similar to how die-to-die inspection is performed.

In addition, the variations in the first images that are greater than other variations in the first images compared to the at least one second image may be detected with relatively high sensitivity. For example, the parameters of the wafer inspection system (e.g. optical image acquisition parameters) and the parameters used to detect the variations that are greater than other variations (e.g., defect detection parameters) may be selected such that the variations that are greater can be detected with relatively high sensitivity. As such, acquiring the first images and the one or more second images and separately comparing the first images to at least one of the second images may essentially include performing a relatively high sensitivity inspection of the wafer. In this manner, as many variations in the first images that are greater than other variations in the first images compared to the at least one second image as possible may be detected, and the number of detected greater variations can then be reduced by performing one or more additional steps described herein (e.g., repeater analysis or other filtering).

As described above, in one embodiment, the first areas correspond to different dies on the wafer, and the at least one second area corresponds to at least two additional dies on the wafer. In one such embodiment, separately comparing the first images acquired for the different first areas to the at least one second image includes comparing one of the different dies to two of the additional dies. In this manner, separately comparing the first images to the at least one second image may include performing a number of different die-to-die comparisons (e.g., two separate comparisons for each of the different first areas being compared, each of the two comparisons may be performed with a different second image). As such, the variations in the first images compared to the at least one second image may be determined in a double arbitration type scheme, in which a test image is compared with two different reference images such that differences between the compared images can be determined as variations in the test image itself or as variations in one of the reference images with greater certainty (compared to a single arbitration scheme in which a test image is compared with one reference image). Therefore, acquiring the first images and the one or more second images and separately comparing the first images to the at least one second image may be performed in a manner similar to how double arbitration die-to-die inspection is performed. In addition, in a double arbitration type scheme, the variations in the first images that are greater than other variations in the first images compared to the at least one second image may be detected with relatively high sensitivity as described above.

In one embodiment, the method includes separately comparing the third images acquired for different third areas to at least one of the one or more second images to determine variation in the third images compared to the at least one second image. Separately comparing the third images acquired for different third areas to at least one of the one or more second images may be performed as described herein.

In addition, the variations in each of the third images that is compared may be separately determined as described further herein. Furthermore, the variations in the third images that are greater than other variations in the third images compared to the at least one second image may be detected with relatively high sensitivity as described further herein.

In embodiments in which the variations in the first images compared to at least one second image are determined by two separate comparisons of a first image to at least two of the second images (e.g., for double arbitration), it may be advantageous to print two columns of second areas on the wafer at the nominal value of the parameter for each column of first areas printed on the wafer at the different values of the parameter. For example, second images of the second areas in columns 18 and 22 shown in FIG. 1 may be acquired and compared to first images of the first areas in column 12. In this manner, first images for each first area in a row may be compared to second images for adjacent second areas in the same row, which may be advantageous because the images can be acquired sequentially and compared as they are acquired. In particular, the images can be acquired as the wafer is scanned and after the comparisons have been performed, the images may be discarded or a substantial portion of the images may be discarded thereby reducing the amount of image data that is stored in order to perform additional steps of the method. In a similar manner, second images of the second areas in columns 30 and 34 shown in FIG. 1 may be acquired and compared to third images of the third areas in column 26. In this manner, comparisons may be performed separately for areas printed within different rows on the wafer.

However, single (or double) arbitration may be performed for any of the first areas using any one (or two) second images acquired for any one (or two) second areas printed anywhere on the wafer. In other words, although the layout of the printed areas shown in FIG. 1 may be advantageous, this layout is not the only layout of the printed areas that can be used to perform the embodiments described herein. For example, although the layout shown in FIG. 1 may advantageously reduce the amount of image data that is stored to perform the method, all of the images acquired for all of the areas printed on the wafer may be stored using systems and methods such as those described in commonly owned U.S. Patent Application Ser. No. 60/974,030 by Bhaskar et al. filed Sep. 20, 2007, which is incorporated by reference as if fully set forth herein. The stored images may then be used in step(s) of the embodiments described herein. The embodiments described herein may include any step(s) of any method(s) described in this patent application.

The method further includes detecting defects on the reticle based on first portions of the first images in which the variations are greater than second portions of the first images and the first portions that are common to two or more of the first images. The defects include crystal growth defects on the reticle. For example, a crystal growth defect on a reticle can print-down on a wafer as a defect. In addition, crystal growth defects on a reticle will be modulated differently at print-down compared to how non-defective portions of the reticle will be modulated. In other words, variations in the first images compared to the at least one second image due to crystal growth defects may be greater than other variations in the first images caused by the modulation itself. Therefore, these defect locations can be detected using the results of the comparisons described above (e.g., die-to-die comparisons).

Although the embodiments described herein can advantageously detect crystal growth defects on a reticle, the embodiments are not limited to crystal growth defects only. For example, the embodiments described herein can also be used for detecting other defect types such as particles and/or chrome damage on reticles. In addition, as long as the reticle defect can cause a soft defect (prints down only intermittently) on a wafer, the embodiments described herein can detect that defect.

The variations in the first images caused by crystal growth defects may also be different for different modulated parameters of the lithography process. For example, the modulation of crystal growth defects may be more sensitive to different values of dose since crystal growth defects particularly affect transmission of light by the reticle. In this manner, the wafer layout shown in FIG. 1 may include at least one column of modulated shots for varying values of dose. However, different values of focus can also cause enough modulation of crystal growth defects such that defects can be detected as described herein. As such, the wafer layout shown in FIG. 1 may also include a column of modulated shots for varying values of focus. Modulating more than one parameter of the lithography process may also provide more experimental data that can be used to detect crystal growth defects with greater certainty.

In one embodiment, the variations include variations in CDs of features in the first images compared to CDs of the features in the at least one second image. For example, crystal growth defects may cause variations in CDs of features adjacent to the crystal growth defects. Therefore, variations in the CDs of features of the reticle printed on the wafer may be used to detect crystal growth defects on the reticle. In addition, a feature that is located adjacent to a crystal growth defect may exhibit more CD variation by modulation of a parameter of the lithography process than a feature that is not located adjacent to a crystal growth defect. In this manner, at any given modulated value of the parameter of the lithography process, a feature that is not located adjacent to a crystal growth defect may exhibit some CD variation due to pattern noise caused by the modulation itself. However, at the same modulated value, a feature that is located adjacent to a crystal growth defect may exhibit some CD variation due to pattern noise caused by the modulation itself but may also exhibit some greater CD variation due to the crystal growth defect. Therefore, CD variation can be used to separate variations in patterns printed on a wafer due to crystal growth defects from other variations in the patterns printed on the wafer due to pattern noise caused by modulation of the lithography process parameter. The variations in the CDs may be determined in any suitable manner using any suitable method and/or algorithm.

Figure 2:
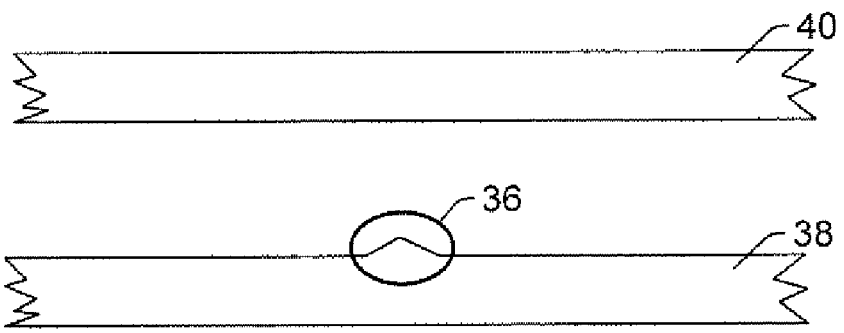
FIG. 2 is a schematic diagram illustrating a plan view of examples of different features printed on a wafer using a nominal value of a parameter of a lithography process and a reticle that has a crystal growth defect near one of the features on the reticle.
Figure 3:
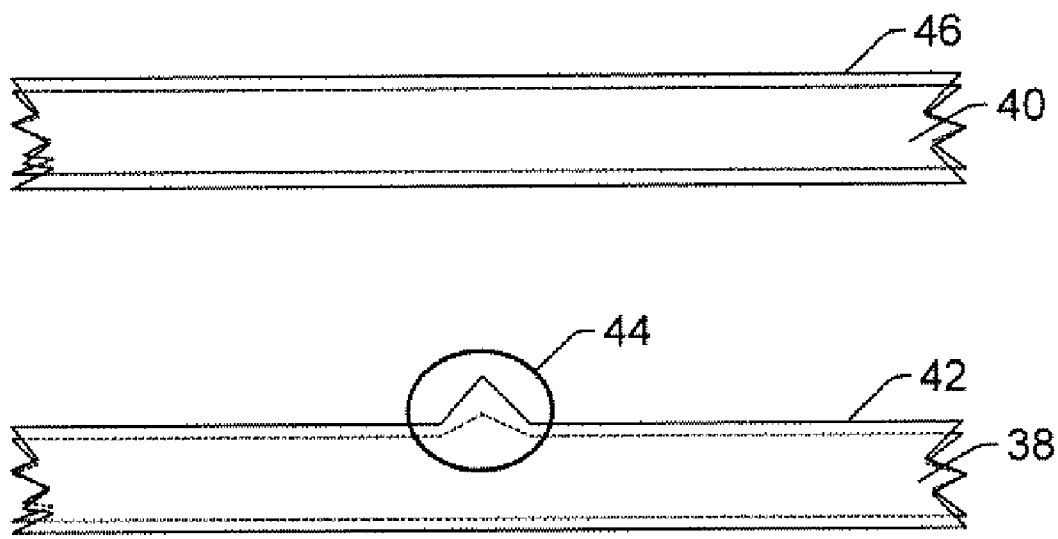
FIG. 3 is a schematic diagram illustrating a plan view of the different features of FIG. 2 printed on the wafer at a different value of the parameter of the lithography process.
Figure 4:
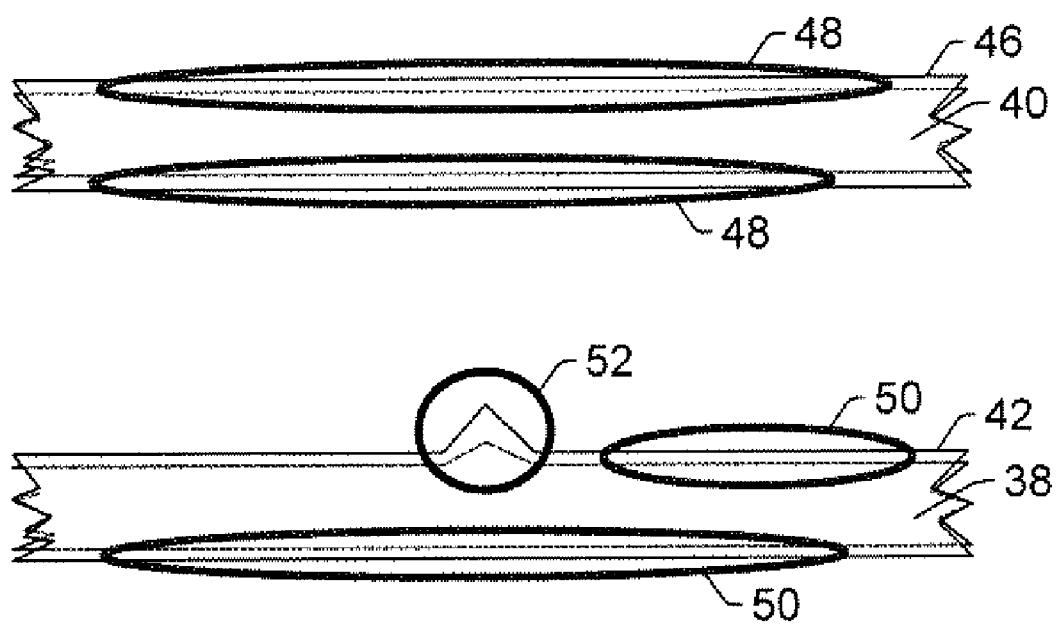
FIG. 4 is a schematic diagram illustrating a plan view of the different features of FIG. 3 overlaid with the different features of FIG. 2 and variations in the critical dimensions (CDs) of the different features of FIG. 3 compared to the CDs of the different features of FIG. 2.

Examples of how a crystal growth defect on a reticle can cause variations in CD of features printed on a wafer are shown in FIGS. 2-4. For example, FIG. 2 illustrates examples of different features printed on a wafer using a nominal value of a parameter of a lithography process. One of the different features printed on the wafer corresponds to a feature on a reticle that is located next to a crystal growth defect, and the other of the different features printed on the wafer corresponds to a feature on a reticle that is not located next to a crystal growth defect. In particular, a crystal growth defect may be located in an open space on a reticle between a main line pattern on the reticle and an assist bar. When the main line pattern is printed on the wafer at a nominal value of a parameter of the lithography process (e.g., at nominal values of dose and focus), the crystal growth defect may cause relatively small protrusion 36 on line pattern 38 printed on the wafer (not shown in FIG. 2). In addition, a crystal growth defect is not present on the reticle between another main line pattern on the reticle and an assist bar. When that main line pattern is printed on the wafer at the nominal value of the parameter of the lithography process (e.g. at nominal values of dose and focus), line pattern 40 may be printed on the wafer. As shown in FIG. 2, line pattern 40 does not include any protrusions.

FIG. 3 illustrates the different features of FIG. 2 printed on the wafer at a different value of a parameter of the lithography process overlaid with the corresponding features of FIG. 2 printed on the wafer at a nominal value of the parameter of the lithography process. For example, line pattern 42 may be printed on the wafer (not shown in FIG. 3) at a different value of a parameter of the lithography process (e.g., at a dose that is lower than nominal thereby producing an under-exposed feature on the wafer). As shown in FIG. 3, relatively small protrusion 44 appears on line pattern 42 at substantially the same location as the relatively small protrusion on line pattern 38 shown in FIG. 2. In addition, line pattern 46 may be printed on the wafer at the same different value of the parameter of the lithography process as line pattern 42. As shown in FIG. 3, both under-exposed line patterns appear differently on the wafer compared to the corresponding line patterns printed at nominal values of focus and dose.

FIG. 4 illustrates the different features shown in FIG. 3 and the variations in the CDs of the different features compared to the CDs of the corresponding different features shown in FIG. 2. In particular, as shown in FIG. 4, at a different value of dose corresponding to under-exposure, feature 46 shows CD variations 48 as compared to feature 40 printed at nominal values of dose and focus. CD variations 48 can be attributed to pattern noise caused by the modulation of the value of dose. In contrast, at the different value of dose corresponding to under-exposure, feature 42 shows CD variations 50 on portions of feature 42 corresponding to portions of the feature on the reticle that are not adjacent to the crystal growth defect and CD variations 52 on the portion of feature 42 corresponding to the portion of the feature on the reticle that is adjacent to the crystal growth defect. CD variations 50 may be attributed to pattern noise caused by the modulation of the value of dose while CD variations 52 can be attributed to the crystal growth defect itself. As shown in FIG. 4, the crystal growth defect causes higher variation in CD when printed at the modulated value of dose compared to the variation in CD due to pattern noise. In this manner, the crystal growth defect shows higher variation when modulated. As such, the defect (protrusion from the pattern) can be detected since the pattern variation signal is stronger as a result of modulation in the exposure condition.

Although crystal growth defects can be detected as described above based on differences in the CD variations across a single feature printed on a wafer, the differences in the variations in the first images may be determined based on multiple features printed on a wafer. For example, the average variation in CD for similar features printed on a wafer at a given modulated value of a parameter of the lithography process can be determined, and the variation in CD for individual portions of the features or individual features can be compared to the average variation to determine those portions or features that exhibit abnormal or outlying CD variations for the modulation. In another example, the expected variation in CD for similar features printed on a wafer at a given modulated value of a parameter of the lithography process can be determined (e.g., experimentally or empirically or based on historical data acquired using other reticles). The variation in the CD for individual portions of features or individual features can then be compared to the expected variation, and any individual portion of a feature or individual feature that exhibits variation outside of the expected variation can be determined to correspond to a portion of a feature or an individual feature on the reticle that is located proximate to a crystal growth defect.

In addition, since crystal growth defects tend to be modulated differently in more than one of the first images (if not all of the first images), separating the first portions in which the variations are greater and which are common to two or more of the first images from the first portions in which the variations are greater but which are not common to two or more of the first images can effectively separate the variations in the first images that are due to crystal growth defects from the variations in the first images that are not due to crystal growth defects.

In this manner, the embodiments described herein can use a PWQ type layout of a reticle printed on a wafer to modulate crystal growth defects on single die reticles to help detect them on print-down wafers with wafer inspection systems (e.g., using a die-to-die comparison). In addition, the embodiments described herein can be used for detecting crystal growth reticle defects or reticle "haze" defects on single die reticles by performing an inspection on a print-down wafer using a PWQ type inspection approach. Therefore, the embodiments described herein can be used for detecting types of defects on reticles that may not be present on the reticles at the time of reticle qualification but appear after the reticles are released for use in manufacturing and have been used for some number of exposures. In this manner, in one embodiment, the method is performed subsequent to release of the reticle to manufacturing and use of the reticle in manufacturing. The method may be performed after a predetermined period of time has elapsed since the release of the reticle to manufacturing. In addition, or alternatively, the method may be performed after the reticle has been used for a predetermined number of exposures.

In one embodiment, detecting the defects includes comparing locations of the first portions within the first images to identify the first portions that are common to the two or more of the first images. For example, the locations of the first portions within the first images may be compared by repeater analysis. In this manner, the inspection data from the modulated columns may be filtered by repeater analysis. As such, repeater analysis may be used after inspection to sort out reticle defect locations from other pattern variation defects caused by the exposure modulations. Repeater analysis may be used after inspection to separate reticle defect locations from other pattern variation defects caused by the modulations because PWQ type exposures will cause a significant amount of pattern noise due to the modulation itself. Although the pattern noise may not repeat from one modulated shot to another, crystal growth defects tend to repeat in each modulated shot. Therefore, repeater analysis can be used to significantly reduce the number of potential reticle defects detected on the wafer.

In another embodiment, detecting the defects includes detecting potential defects on the reticle based on the first portions and the first portions that are common to the two or more of the first images and reviewing locations on the wafer corresponding to the first portions that are common to the two or more of the first images to determine if the potential defects are real defects. For example, the potential defects may be identified as the first portions of the first images in which the variations are greater than second portions of the first images. In addition, identifying the potential defects may include filtering the first portions of the first images in which the variations are greater than second portions of the first images (e.g., using repeater analysis) to identify the first portions that are common to two or more of the first images as the potential defects. Therefore, the potential defects may be identified as the repeaters in the first images. The repeaters may then be reviewed optically to eliminate some of the potential reticle defects as not real reticle-related defects. Optical review of the repeaters may be performed in any suitable manner using any suitable optical wafer defect review system. The potential reticle defects identified by optical review may then be reviewed using a scanning electron microscope (SEM) to determine if the potential defects are real reticle-related defects. SEM review of the potential reticle defects may be performed in any suitable manner using any suitable SEM wafer defect review system. Optical review of the repeaters may be performed before SEM review to reduce the number of potential reticle defects that are reviewed by SEM. However, if the number of repeaters in the first images is relatively low, optical review may not be performed before SEM review of the locations on the wafer corresponding to the repeaters in the first images.

As described above, therefore, repeater analysis may be performed on the first portions of the first images in which the variations are greater than second portions of the first images to identify the first portions that are common to two or more of the first images. Those first portions that are common to two or more of the first images may then be analyzed by defect review to identify potential and/or real reticle defects. In this manner, if the first portions of the first images in which the variations are greater than the second portions of the first images are relatively large in number, repeater analysis may be used to reduce the number of the locations on the wafer corresponding to the first portions that are reviewed to identify the potential and/or real reticle defects. However, if the first portions of the first images in which the variations are greater than the second portions of the first images are relatively small in number, review may be performed for all of the locations on the wafer corresponding to the first portions to identify the potential and/or real reticle defects.

In an additional embodiment, detecting the defects includes comparing locations of the first portions in the first images to locations of patterned features in the first images that correspond to patterned features on the reticle to separate the first portions that correspond to the crystal growth defects from the first portions that correspond to other defects on the reticle. For example, crystal growth defects tend to cause defects on a wafer when the crystal growth defects are located in transmissive portions of the reticle. In addition, since crystal growth defects can cause variations in the transmission of light through the reticle regardless of the positions of features on the reticle relative to the positions of the crystal growth defects, the crystal growth defects may cause defects on the wafer that are spaced from other features printed on the wafer. For example, a crystal growth defect in an open space on a reticle and spaced from opaque features on the reticle may cause a defect on the wafer that is spaced from other features printed on the wafer. Therefore, if a location of a first portion of the first images is spaced from patterned features in the first images, that location can be identified as a location of a potential crystal growth defect. The potential crystal growth defect can be confirmed as an actual crystal growth defect as described herein (e.g., by optical and/or SEM review).

In a further embodiment, detecting the defects includes performing design based binning (DBB) of the first portions to separate the crystal growth defects from other defects on the reticle. For example, DBB can be performed to separate pattern variations from reticle defect locations. In particular, DBB generally involves comparing the patterns located proximate to potential defect locations to identify defects that appear within the same portions of the pattern printed on the wafer or at substantially the same within-pattern position. In this manner, DBB may be used to identify the first portions of the first images that appear within the same portions of the pattern or at substantially the same within-pattern position thereby identifying the first portions that repeat across modulations and are therefore indicative of potential reticle crystal growth defects. DBB can be performed as described in commonly owned U.S. patent application Ser. No. 11/561,659 by Zafar et al. filed Nov. 20, 2006, which published as U.S. Patent Application Publication No. 2007/0288219 on Dec. 13, 2007, and Ser. No. 11/561,735 by Kulkarni et al. filed Nov. 20, 2006, which published as U.S. Patent Application Publication No. 2007/0156379 on Jul. 5, 2007, which are incorporated by reference as if fully set forth herein. The embodiments described herein may include any step(s) of any method(s) described in these patent applications. In this manner, DBB can be used as a form of repeater analysis. Those first portions that are determined to repeat by DBB are therefore indicative of locations of potential crystal growth defects on the reticle, which can be confirmed as actual crystal growth defects as described herein (e.g., by optical and/or SEM review).

In one embodiment, the method includes detecting the defects on the reticle based on first portions of the third images in which the variations are greater than second portions of the third images and the first portions of the third images that are common to two or more of the third images. Detecting the defects on the reticle based on the first portions of the third images in which the variations are greater than second portions of the third images and that are common to two or more of the third images may be performed as described herein. In addition, the steps described above may be performed using a combination of the first portions of the first images and the first portions of the third images. For example, repeater analysis may be performed collectively on the first portions of the first and third images. Those first portions of the first and third images that are determined to repeat may be identified as corresponding to locations of potential crystal growth defects on the reticle. The potential crystal growth defects may be identified as actual crystal growth defects as described herein (e.g., by optical and/or SEM review).

In another embodiment, the defects do not include defects in patterned features on the reticle. For example, although the first portions of the first images are determined based on variations in the first images such as variations in CD of features in the images, the variations in the first images may be caused by crystal growth defects instead of defects in patterned features themselves formed on the reticle. In addition, defects in the patterned features themselves may be modulated differently than crystal growth defects. Therefore, crystal growth defects can be detected by the methods described herein based on the variations in the first portions of the first images without also detecting defects in the patterned features formed on the reticle. In addition, if some defects in patterned features formed on the reticle have been determined to be "acceptable" prior to qualification of the reticle (e.g., because the defects will not affect yield of devices fabricated using the reticle), information about those acceptable defects may be used to separate defects in the patterned features from other defects detected by the embodiments. Examples of how information about acceptable defects may be used to separate acceptable defects from other defects detected during post-qualification inspection of a reticle are described in commonly owned U.S. patent application Ser. No. 11/139,151 filed May 27, 2005 by Volk, which is incorporated by reference as if fully set forth herein. The embodiments described herein may include any step(s) of any method(s) described in this patent application.

Although many reticle inspection methods are designed for detecting defects in patterned features as formed on reticles, since the embodiments described herein can be used to detect crystal growth defects on a reticle, the embodiments will generally be used after the reticle has been qualified and released for manufacturing. In this manner, when the embodiments described herein are used to detect defects on reticles, the reticles will generally include no defects of interest in the patterned features formed on the reticle. For example, prior to qualification of the reticle, any defects in the patterned features formed on the reticle may be repaired or determined to be acceptable defects. Therefore, after qualification of the reticle, defects in the patterned features themselves on the reticle are generally not of interest to a user. Instead, defects on the reticle such as crystal growth defects that may appear on the reticle after qualification are of interest to the user during post-qualification inspection since those defects were not previously detected and/or determined to be acceptable and may adversely affect the yield of devices fabricated using the reticle. In this manner, the embodiments described herein may be particularly advantageous for inspection of qualified reticles since the embodiments can detect defects that appear after qualification without detecting defects that may have been present prior to qualification and are still on the reticle because they have been deemed to be acceptable defects.

In an additional embodiment, the crystal growth defects include crystal growth defects that print on the wafer at the nominal value of the parameter. In another embodiment, the defects appear in the first images and the one or more second images. For example, the embodiments described herein can be used to detect reticle defects using a die-to-die type comparison even though the reticle defects may be printed in all dies that are compared. In particular) as described above, crystal growth defects will print differently at modulated values of a parameter of a lithography process as compared to how the crystal growth defects will print at a nominal value of the parameter. In particular, modulation of the parameter of the lithography process will cause a crystal growth defect to produce more variation in the area printed on the wafer corresponding to the location of the crystal growth defect than at a nominal value of the parameter. Therefore, crystal growth defects will produce differences between images of areas on the wafer in which the reticle is printed at modulated values compared to images of areas on the wafer in which the reticle is printed at a nominal value of the parameter. As described further herein, the differences in the images caused by crystal growth defects can be separated from other differences between the images caused by pattern variations due to modulation based on comparisons between the differences themselves and based on whether or not the differences repeat for two or more modulated values.

In a further embodiment, the crystal growth defects include crystal growth defects that will print in almost 100% of the dies printed on wafers with the reticle at the nominal value of the parameter. In this manner, the embodiments described herein can be used to detect "hard" crystal growth defects on a single die reticle by inspecting a PWQ style print-down wafer and performing a PWQ type analysis. In particular, a "hard" crystal growth defect can be generally defined as a crystal growth defect that causes failure substantially consistently. In other words, a "hard" crystal growth defect is a defect that prints down consistently at nominal exposure conditions. In this manner, a hard crystal growth defect on a single die reticle will affect nearly 100% of the dies on a wafer and thereby can cause zero yield. In contrast, a "soft" crystal growth defect can be generally defined as a crystal growth defect that is not consistent in that it may not always print on the wafer. Although the embodiments described herein can advantageously detect hard crystal growth defects, the embodiments described herein can also detect soft crystal growth defects that appear in at least two images of the areas on the wafer in which the reticle is printed with modulated values of the parameter of the lithography process.

In contrast to the embodiments described herein, some currently used methods for detecting defects on single die reticles include using a reticle inspection tool, such as those commercially available from KLA-Tencor, San Jose, Calif., to inspect the reticle directly. For example, reticle inspection tools may detect light transmitted and reflected by a reticle to detect contamination defects on the reticle. Such reticle inspection systems are advantageous in that they can inspect reticles without any information about the pattern on the reticle, can inspect both single die reticles and multi-die reticles, and can inspect all areas on reticles including border areas and scribe areas. However, disadvantages of such methods is the relatively high cost of ownership and relatively slow throughput of reticle inspection tools. Therefore, it would be advantageous to detect defects on single die reticles using other inspection tools. For example, a reticle can be printed on a wafer and then the wafer can be inspected using die-to-die comparisons to determine if any defects on the wafer correspond to defects on the reticle. In such inspection, a defect is detected if the comparison of one die to another shows a bigger difference at a defective location vs. the background pattern difference. However, due to the nature of single die reticles, reticle defects will be printed on every die (which is one full reticle field) on the wafer. Therefore, if inspection of the wafer uses die-to-die comparisons to identify defective locations, the wafer inspection system will not be able to detect defects on a single die reticle since they will look the same on every die on the wafer.

However, as described further herein, since reticle crystal growth defects will be modulated differently at modulated values of a parameter of the lithography process compared to the nominal value of the parameter, the reticle crystal growth defects can be detected by the embodiments described herein without using a reticle inspection system. In particular, none of the steps described herein are performed using a reticle inspection system. In this manner, the embodiments described herein may be performed without reticle inspection systems. Therefore, the embodiments described herein provide a significant cost saving as compared to performing inspection of the reticle on a reticle inspection system. For example, one reticle inspection system may cost on the order of 10 million US dollars. In addition, single die reticles are relatively common for engineering devices and microprocessors. However, many wafer fabrication facilities do not have any (or adequate) reticle inspection systems, which has been the only system capable of inspecting single die reticles for crystal growth defects. As such, for a wafer fabrication facility that does not have any reticle inspection systems or has limited reticle inspection system capacity, the embodiments described herein may be used to identify reticle defects using a wafer inspection system. Therefore, the embodiments described herein can be extremely valuable to users of single die reticles.

The embodiments described herein may also include storing results of one or Do more steps of one or more methods described herein in a storage medium. The results may include any of the results described herein. The results may be stored in any manner known in the art. The storage medium may include any suitable storage medium known in the art. After the results have been stored, the results can be accessed in the storage medium and used by any of the method or system embodiments described herein, any other method, or any other system. Furthermore, the results may be stored "permanently," "semi-permanently," temporarily, or for some period of time. For example, the storage medium may be random access memory (RAM), and the results may not necessarily persist indefinitely in the storage medium.

Another embodiment relates to a computer-implemented method for detecting defects on a reticle. The computer-implemented method includes acquiring first images of first areas on a wafer. The first images are generated by a wafer inspection system. Acquiring the first images may be performed using the wafer inspection system. For example, acquiring the first images may include using the wafer inspection system to scan light over the wafer and to generate output responsive to light reflected from the wafer that is detected by the wafer inspection system during scanning. In this manner, acquiring the first images may include scanning the wafer. However, acquiring the first images does not necessarily include scanning the wafer. For example, acquiring the first images may include acquiring the first images from a storage medium in which the first images have been stored (e.g., by the wafer inspection system). Acquiring the first images from the storage medium may be performed in any suitable manner, and the storage medium from which the first images are acquired may include any of the storage media described herein. The first images may include any of the first images described herein. The wafer inspection system may include any of the wafer inspection systems described herein. In addition, the wafer inspection system may generate the first images in any suitable manner.

A reticle is printed in different first areas using different values of a parameter of a lithography process. The reticle may be printed in the different first areas as described further herein. The first areas may be arranged on the wafer according to any of the embodiments described herein. The parameter of the lithography process may be any of the parameters of the lithography process described herein. The different values of the parameter may include any of the different values described herein. The reticle is a single die reticle. The single die reticle may be configured as described herein.

The computer-implemented method also includes acquiring one or more second images of at least one second area of the wafer. The one or more second images are generated by the wafer inspection system. Acquiring the one or more second images of the at least one second area of the wafer may be performed as described herein. The one or more second images may include any of the second image(s) described herein. The wafer inspection system may be configured to generate the one or more second images as described herein or in any other suitable manner. The reticle is printed in the at least one second area using a nominal value of the parameter. The reticle may be printed in the at least one second area as described further herein. The at least one second area may be arranged on the wafer as described herein. The nominal value of the parameter may include any of the nominal values of the parameter described herein.

In addition, the computer-implemented method includes separately comparing the first images acquired for different first areas to at least one of the one or more second images to determine variation in the first images compared to the at least one second image. Separately comparing the first images acquired for the different first areas to at least one of the one or more second images may be performed as described further herein. The variation in the first images compared to the at least one second image determined by the separately comparing step may include any of the variations described herein.

The computer-implemented method further includes detecting defects on the reticle based on first portions of the first images in which the variations are greater than second portions of the first images and the first portions that are common to two or more of the first images. Detecting the defects may be performed as described further herein. The defects include crystal growth defects on the reticle. The crystal growth defects may include any of the crystal growth defects described herein. The computer-implemented method may include any other step(s) of any other method(s) described herein.

Figure 5:
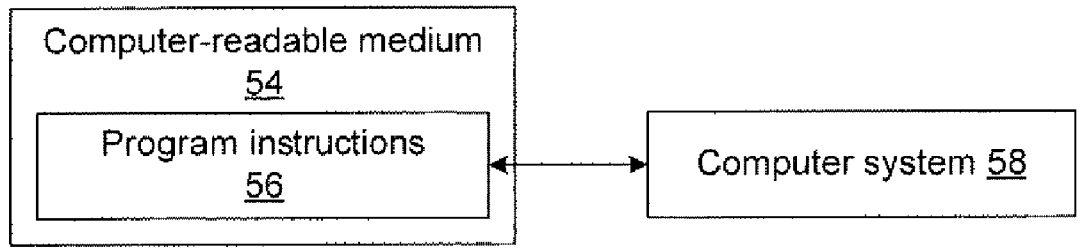
FIG. 5 is a block diagram illustrating one embodiment of a computer-readable medium that includes program instructions executable on a computer system for performing a computer-implemented method for detecting defects on a reticle.

An additional embodiment relates to a computer-readable medium that includes program instructions executable on a computer system for performing a computer-implemented method for detecting defects on a reticle. One such embodiment is shown in FIG. 5. For example, as shown in FIG. 5, computer-readable medium 54 includes program instructions 56 executable on computer system 58 for performing a computer-implemented method for detecting defects on a reticle. The computer-implemented method may include any of the computer-implemented method(s) described herein.

Program instructions 56 implementing methods such as those described herein may be transmitted over or stored on computer-readable medium 54. The computer-readable medium may be a storage medium such as a read-only memory, a RAM, a magnetic or optical disk, a magnetic tape, or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 58 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 6:
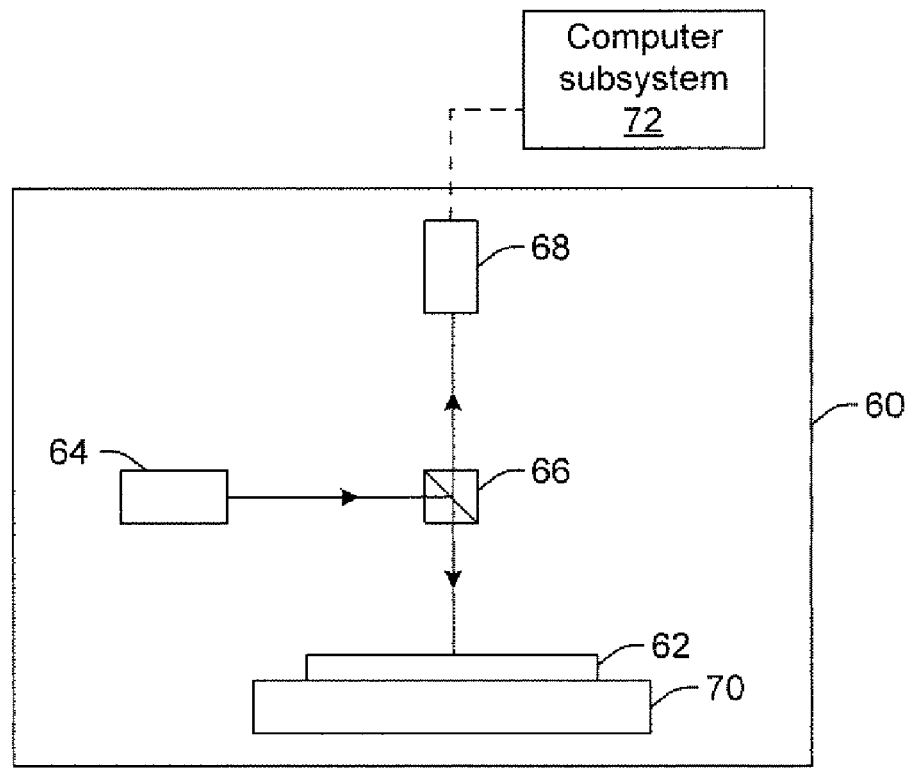
FIG. 6 is a schematic diagram illustrating a side view of one embodiment of a wafer inspection system configured to detect defects on a reticle.

A further embodiment relates to a wafer inspection system configured to detect defects on a reticle. FIG. 6 illustrates one embodiment of a wafer inspection system configured to detect defects on a reticle. The wafer inspection system includes inspection subsystem 60 configured to acquire first images of first areas (not shown in FIG. 6) on wafer 62 and one or more second images of at least one second area (not shown in FIG. 6) on wafer 62. The inspection subsystem includes light source 64 that is configured to generate light. Light source 64 may include any suitable light source that is configured to generate any suitable light. The inspection subsystem also includes beam splitter 66 that is configured to direct the light generated by the light source to wafer 62 at a substantially normal angle of incidence. Beam splitter 66 may be any suitable beam splitter known in the art. In this manner, light may be directed to the wafer at a substantially normal angle of incidence. However, the inspection subsystem may be configured to direct the light to the wafer at any other suitable angle of incidence.

The inspection subsystem also includes detector 68. Light reflected by the wafer passes through beam splitter 66 and is detected by detector 68. Detector 68 may include any suitable imaging detector. In this manner, the detector may generate and acquire the first images and the one or more second images. The first images may include any of the first images described herein. The one or more second images may include any of the one or more second images described herein.

The inspection subsystem may also include stage 70 configured to support wafer 62. Stage 70 may also be configured to move wafer 62 with respect to the optical elements of the inspection subsystem such that the inspection subsystem can scan the wafer while acquiring the first images and the one or more second images. The inspection subsystem may scan the wafer as described further herein. The stage may include any suitable mechanical assembly or robotic assembly and may be configured to move the wafer in any suitable manner. The inspection subsystem may also include any other suitable optical elements known in the art.

A reticle is printed in different first areas on the wafer using different values of a parameter of a lithography process. The reticle may be printed in the different first areas as described further herein. The first areas may be arranged on the wafer as described further herein. The parameter of the lithography process may be any of the parameters of the lithography process described herein. The different values of the parameter may include any of the different values described herein. The reticle is printed in the at least one second area on the wafer using a nominal value of the parameter. The reticle may be printed in the at least one second area as described further herein. The at least one second area may be arranged on the wafer as described further herein. The nominal value of the parameter may include any of the nominal values described herein. The reticle is a single die reticle. The single die reticle may be configured as described herein.

The wafer inspection system also includes computer subsystem 72 configured to separately compare the first images acquired for different first areas to at least one of the one or more second images to determine variation in the first images compared to the at least one second image. For example, computer subsystem 72 may be coupled to detector 68 (e.g., by a transmission medium shown by the dashed line in FIG. 6, which may include any suitable transmission medium known in the art) such that the computer subsystem can acquire the first images and the one or more second images from the detector. The computer subsystem may be configured to separately compare the first images acquired for the different first areas to the at least one of the one or more second images as described further herein. The variation in the first images compared to the at least one second image determined by the computer subsystem may include any of the variations described herein.

The computer subsystem is also configured to detect defects on the reticle based on first portions of the first images in which the variations are greater than second portions of the first images and the first portions that are common to two or more of the first images. The computer subsystem may be configured to detect the defects as described further herein. The defects include crystal growth defects on the reticle. The crystal growth defects may include any of the crystal growth defects described herein.

The computer subsystem may be configured to perform any other step(s) of any method embodiment(s) described herein. The computer subsystem may be further configured as described herein. For example, the computer subsystem may include any of the computer systems described herein. The inspection subsystem may also be further configured as described herein. Furthermore, the system may be further configured as described herein.

It is noted that FIG. 6 is provided herein to generally illustrate one configuration of an inspection subsystem that may be included in the wafer inspection system embodiments described herein. Obviously, the inspection subsystem configuration described herein may be altered to optimize the performance of the inspection subsystem as is normally performed when designing a commercial wafer inspection system. In addition, the wafer inspection systems described herein may be implemented using an existing wafer inspection system (e.g., by adding functionality described herein to an existing wafer inspection system) such as the 28xx series of tools that are commercially available from KLA-Tencor. For some such systems, the methods described herein may be provided as optional functionality of the wafer inspection system (e.g., in addition to other functionality of the wafer inspection system). Alternatively, the system described herein may be designed "from scratch" to provide a completely new wafer inspection system.

Further modifications and alternative embodiments of various aspects of the invention may be apparent to those skilled in the art in view of this description. For example, methods and systems for detecting defects on a reticle are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for detecting defects on a reticle, comprising:
   printing a reticle in first areas on a wafer and at least one second area on the wafer, wherein the reticle is printed in different first areas using different values of a parameter of a lithography process, wherein the reticle is printed in the at least one second area using a nominal value of the parameter, and wherein the reticle is a single die reticle;
   acquiring first images of the first areas and one or more second images of the at least one second area using a wafer inspection system;
   separately comparing the first images acquired for different first areas to at least one of the one or more second images to determine variation in the first images compared to the at least one second image; and
   detecting defects on the reticle based on first portions of the first images in which the variations are greater than second portions of the first images and the first portions that are common to two or more of the first images, wherein the defects comprise crystal growth defects on the reticle.

2. The method of claim 1, wherein the parameter comprises dose.

3. The method of claim 1, wherein the parameter comprises focus.

4. The method of claim 1, further comprising printing the reticle in third areas on the wafer, wherein the reticle is printed in different third areas using different values of an additional parameter of the lithography process, and wherein the method further comprises acquiring third images of the third areas using the wafer inspection system, separately comparing the third images acquired for different third areas to at least one of the one or more second images to determine variation in the third images compared to the at least one second image, and detecting the defects on the reticle based on first portions of the third images in which the variations are greater than second portions of the third images and the first portions of the third images that are common to two or more of the third images.

5. The method of claim 4, wherein the parameter comprises dose, and wherein the additional parameter comprises focus.

6. The method of claim 1, wherein the first areas are arranged in one column on the wafer, and wherein the at least one second area is arranged in one or more additional columns on the wafer.

7. The method of claim 1, wherein the first areas correspond to different dies on the wafer, wherein the at least one second area corresponds to at least one additional die on the wafer, and wherein separately comparing the first images acquired for the different first areas to the at least one second image comprises comparing one of the different dies to one of the at least one additional die.

8. The method of claim 1, wherein the first areas correspond to different dies on the wafer, wherein the at least one second area corresponds to at least two additional dies on the wafer, and wherein separately comparing the first images acquired for the different first areas to the at least one second image comprises comparing one of the different dies to two of the additional dies.

9. The method of claim 1, wherein the variations comprise variations in critical dimensions of features in the first images compared to critical dimensions of the features in the at least one second image.

10. The method of claim 1, wherein detecting the defects comprises comparing locations of the first portions within the first images to identify the first portions that are common to the two or more of the first images.

11. The method of claim 1, wherein detecting the defects comprises detecting potential defects on the reticle based on the first portions and the first portions that are common to the two or more of the first images and reviewing locations on the wafer corresponding to the first portions that are common to the two or more of the first images to determine if the potential defects are real defects.

12. The method of claim 1, wherein detecting the defects comprises comparing locations of the first portions in the first images to locations of patterned features in the first images that correspond to patterned features on the reticle to separate the first portions that correspond to the crystal growth defects from the first portions that correspond to other defects on the reticle.

13. The method of claim 1, wherein detecting the defects comprises performing design based binning of the first portions to separate the crystal growth defects from other defects on the reticle.

14. The method of claim 1, wherein the method is performed subsequent to release of the reticle to manufacturing and use of the reticle in manufacturing.

15. The method of claim 1, wherein the defects do not comprise defects in patterned features on the reticle.

16. The method of claim 1, wherein the crystal growth defects comprise crystal growth defects that print on the wafer at the nominal value of the parameter.

17. The method of claim 1, wherein the crystal growth defects comprise crystal growth defects that will print in almost 100% of the dies printed on wafers with the reticle at the nominal value of the parameter.

18. The method of claim 1, wherein the defects appear in the first images and the one or more second images.

19. A computer-implemented method for detecting defects on a reticle, comprising:
   acquiring first images of first areas on a wafer, wherein the first images are generated by a wafer inspection system, wherein a reticle is printed in different first areas using different values of a parameter of a lithography process, and wherein the reticle is a single die reticle;
   acquiring one or more second images of at least one second area on the wafer, wherein the one or more second images are generated by the wafer inspection system, and wherein the reticle is printed in the at least one second area using a nominal value of the parameter;
   separately comparing the first images acquired for different first areas to at least one of the one or more second images to determine variation in the first images compared to the at least one second image; and
   detecting defects on the reticle based on first portions of the first images in which the variations are greater than second portions of the first images and the first portions that are common to two or more of the first images, wherein the defects comprise crystal growth defects on the reticle.

20. A wafer inspection system configured to detect defects on a reticle, comprising:
   an inspection subsystem configured to acquire first images of first areas on a wafer and one or more second images of at least one second area on the wafer, wherein a reticle is printed in different first areas using different values of a parameter of a lithography process, wherein the reticle is printed in the at least one second area using a nominal value of the parameter, and wherein the reticle is a single die reticle; and
   a computer subsystem configured to separately compare the first images acquired for different first areas to at least one of the one or more second images to determine variation in the first images compared to the at least one second image and to detect defects on the reticle based on first portions of the first images in which the variations are greater than second portions of the first images and the first portions that are common to two or more of the first images, wherein the defects comprise crystal growth defects on the reticle.

* * * * *